United States Patent
Beaudry

(10) Patent No.: US 7,008,392 B2
(45) Date of Patent: Mar. 7, 2006

(54) HEMOSTATIC CLEANSING SWAB

(75) Inventor: Scott Alexander Beaudry, Kendall Park, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 272 days.

(21) Appl. No.: 10/608,506

(22) Filed: Jun. 27, 2003

(65) Prior Publication Data

US 2004/0267180 A1 Dec. 30, 2004

(51) Int. Cl.
A61M 35/00 (2006.01)
(52) U.S. Cl. .......................... 604/1; 604/309
(58) Field of Classification Search ............ 604/1, 604/289, 290, 306, 309, 310, 2, 3; 206/438
See application file for complete search history.

(56) References Cited

U.S. PATENT DOCUMENTS

| 2,423,707 | A | * | 7/1947 | Kenyon et al. | 139/426 R |
| 2,688,586 | A | * | 9/1954 | Eberl et al. | 424/445 |
| 2,800,673 | A | * | 7/1957 | Lazisky | 401/188 R |
| 3,324,855 | A | * | 6/1967 | Heimlich | 604/3 |
| 3,327,706 | A | * | 6/1967 | Watson, Sr. | 604/309 |
| 3,343,540 | A | * | 9/1967 | Siegel | 604/1 |
| 3,586,380 | A | | 6/1971 | Galib-bey | |
| 3,876,314 | A | * | 4/1975 | Nehring | 401/133 |
| 3,891,331 | A | * | 6/1975 | Avery | 401/132 |
| 4,173,978 | A | * | 11/1979 | Brown | 604/3 |
| 4,206,843 | A | * | 6/1980 | Rainey | 206/216 |
| 4,225,254 | A | * | 9/1980 | Holberg et al. | 401/119 |
| 4,390,519 | A | * | 6/1983 | Sawyer | 424/447 |
| 4,404,970 | A | * | 9/1983 | Sawyer | 424/400 |
| 4,551,100 | A | * | 11/1985 | Fischer | 433/218 |
| 4,730,949 | A | * | 3/1988 | Wilson | 401/132 |
| 4,740,194 | A | * | 4/1988 | Barabino et al. | 604/3 |
| 5,009,652 | A | * | 4/1991 | Morgan et al. | 604/385.01 |
| 5,100,028 | A | * | 3/1992 | Seifert | 222/107 |
| 5,827,307 | A | * | 10/1998 | Tipton | 606/160 |
| 6,283,933 | B1 | * | 9/2001 | D'Alessio et al. | 604/3 |
| 2001/0031221 | A1 | * | 10/2001 | Wu et al. | 422/28 |
| 2002/0169476 | A1 | * | 11/2002 | Cohen | 606/214 |
| 2004/0138606 | A1 | * | 7/2004 | McPheeters et al. | 604/1 |

FOREIGN PATENT DOCUMENTS

EP 0 363 533 4/1990

* cited by examiner

Primary Examiner—Tatyana Zalukaeva
Assistant Examiner—Paula L. Craig

(57) ABSTRACT

The present invention relates to a swab for treating wounds. The swab comprises a stick to one end of which is attached a wound treating element. The wound treating element has a wound cleansing element and a hemostat-containing element. A reservoir is provided for retaining a cleansing or other solution in fluid communication with the wound cleaning element.

15 Claims, 4 Drawing Sheets

HEMOSTATIC CLEANSING SWAB

BACKGROUND OF THE INVENTION

1. Field of the Invention

The present invention relates to a swab for treating wounds. The swab has a stick and a wound treating element which comprises a wound cleansing portion for cleansing a wound and a hemostatic portion for effecting hemostasis of a wound. The swab has a reservoir for containing a liquid, the reservoir being in fluid communication with the wound cleansing portion. The reservoir for containing liquid is closed prior to use by a frangible seal.

2. Description of the Prior Art

Wounds, such as cuts and scrapes, are prone to infection. It is common practice to clean a wound to help reduce the risk of infection. Various wound cleansing solutions are commercially available. These solutions can be applied directly to the wound, for example, by spraying. Alternatively, a gauze pad or the like can be used to apply the cleansing solution. Wound cleansing pads are also commercially available. These pads typically have a soft padded side that is loaded with a cleansing solution and a somewhat rougher plastic side opposed to the soft side. The plastic side is used to debride the wound, while the padded side is used to gently cleanse the wound.

It is sometimes difficult to stop a wound from bleeding. In such event, a hemostatic agent is applied to the wound to effect hemostasis, i.e., to arrest the bleeding. There are many commercially available hemostatic agents. Among these is calcium alginate. Calcium alginate has been incorporated into the wound-contacting pad of a conventional adhesive bandage. The alginate reacts with the blood from a bleeding wound and coagulates the blood, thereby stopping the bleeding. A hemostatic adhesive bandage has been marketed heretofore under the designation BAND-AID® Brand QUICK STOP® Adhesive Bandage.

Wound cleansing implements are known in the art and are disclosed, for example, in U.S. Pat. Nos. 3,324,855 and 5,100,028, the teachings of which are hereby incorporated by reference.

Although conventional wound cleansers and hemostats are effective for their intended purpose, it is somewhat inconvenient to have separate implements for cleaning the wound and stopping the bleeding from the wound. Accordingly, there is a need for a single implement that provides a first portion for cleansing a wound and a second portion for effecting hemostasis of the wound.

SUMMARY OF THE INVENTION

The present invention provides a hemostatic cleansing swab which includes a stick, a wound treating element and a reservoir for containing a liquid. The stick has a proximal portion which serves as a handle during use of the swab and a distal portion. The wound treating element is secured to the distal portion of the stick and comprises a wound cleaning element and an element for effecting hemostasis of a wound. The reservoir is in fluid communication with the wound cleansing element.

In a preferred embodiment, the stick comprises a hollow region which forms the reservoir for containing a liquid. The stick is closed at its proximal end to provide a liquid tight seal. The reservoir for containing a liquid is sealed in the distal portion of the stick by a liquid-tight, frangible seal. In one embodiment contemplated by the invention, the frangible seal is located at the distal end of the stick. In this instance, substantially the entire length of the hollow interior of the stick is available to contain a liquid. If desired, the frangible seal may be located a distance away from the distal end of the stick in the direction of the proximal end of the stick.

Preferably, the reservoir contains a liquid cleansing composition for cleansing a wound. At the time of use, the frangible seal is broken, thus allowing the liquid cleansing composition to flow to the wound cleansing element of the swab.

Preferably, the wound cleansing element and the hemostat-containing element are secured one to the other. In this instance, a thin, liquid-impervious film may be placed between the adjoining surfaces of the wound cleansing element and the hemostat-containing element. The presence of this film prevents the liquid cleansing composition released to the wound cleansing element from undesirably flowing to the hemostat-containing element of the swab.

BRIEF DESCRIPTION OF THE DRAWINGS

The invention will be more fully understood and further advantages will become apparent when reference is made to the following detailed description of the invention and the accompanying drawings in which.

DETAILED DESCRIPTION OF PREFERRED EMBODIMENTS

Figure 1:
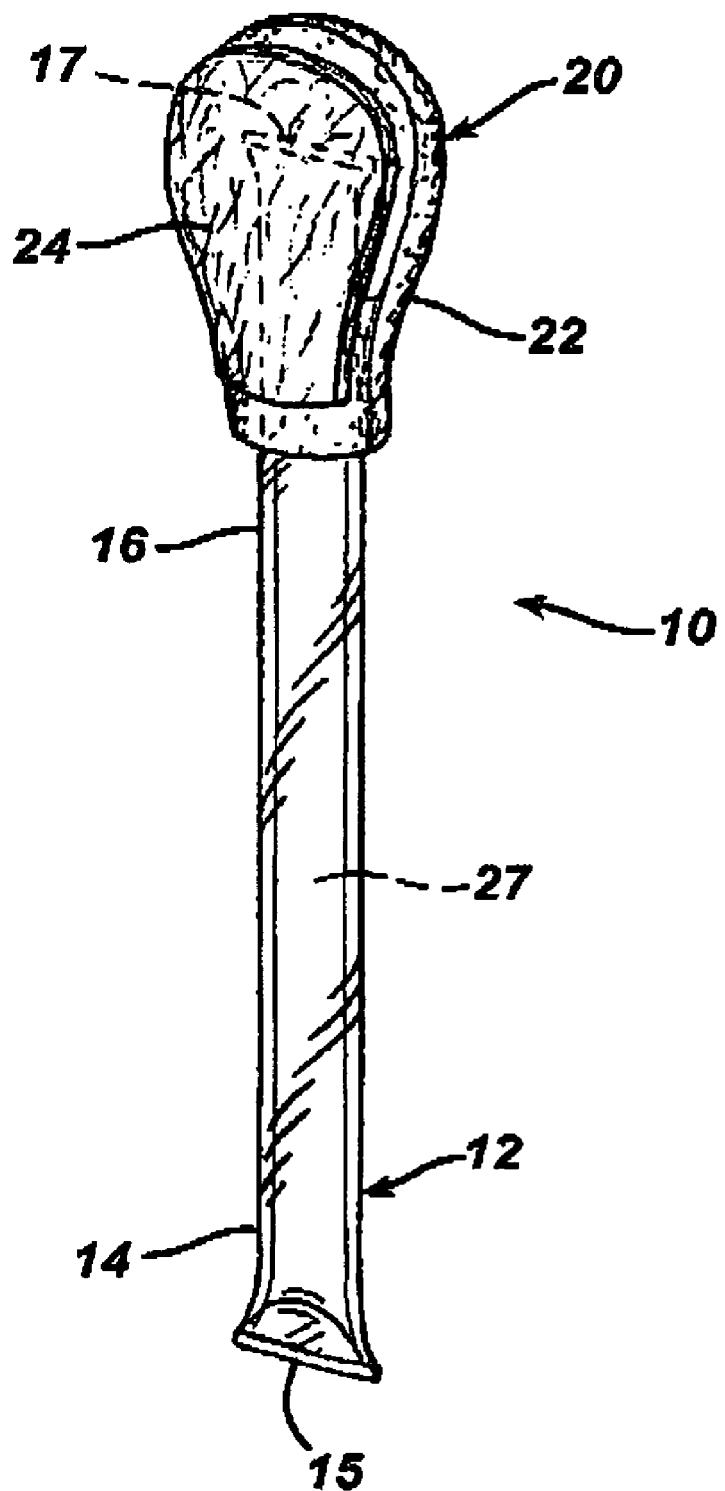
FIG. 1 is a perspective view of a preferred embodiment of a hemostatic cleansing swab in accordance with the teaching of the present invention.
Figure 2:
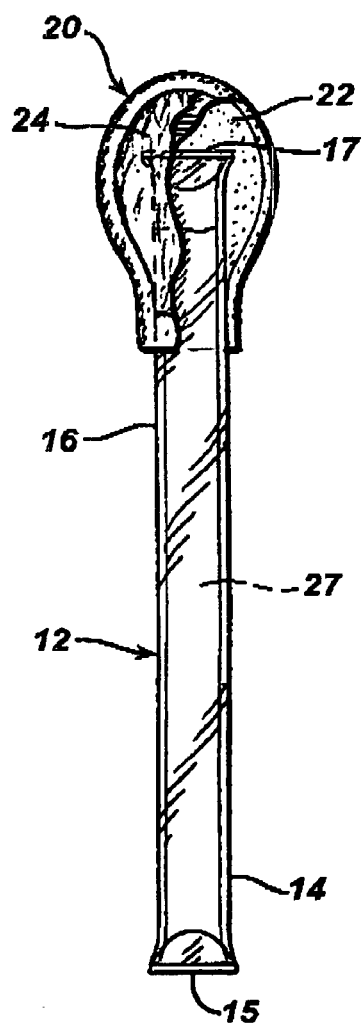
FIG. 2 is a front elevational view, with portions cut away, of the swab of FIG. 1.

Referring now to the appended drawings, FIGS. 1–5 show a preferred embodiment of a hemostatic cleansing swab in accordance with the teachings of the present invention.

Hemostatic cleansing swab 10 comprises a hollow stick 12 and a wound treating element 20. Stick 12 is generally elongated and has a proximal portion 14, a proximal end 15, a distal portion 16 and a distal end 17. Proximal portion 14 of stick 12 serves as a handle during use of the swab.

Figure 3:
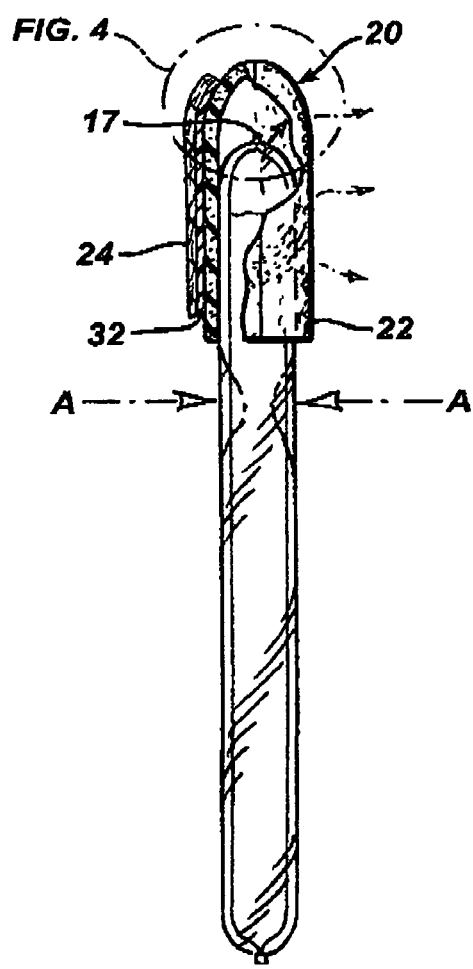
FIG. 3 is a side elevational view, with certain portions cut away and other portions in cross-section, of the swab of FIG. 1.
Figure 4:
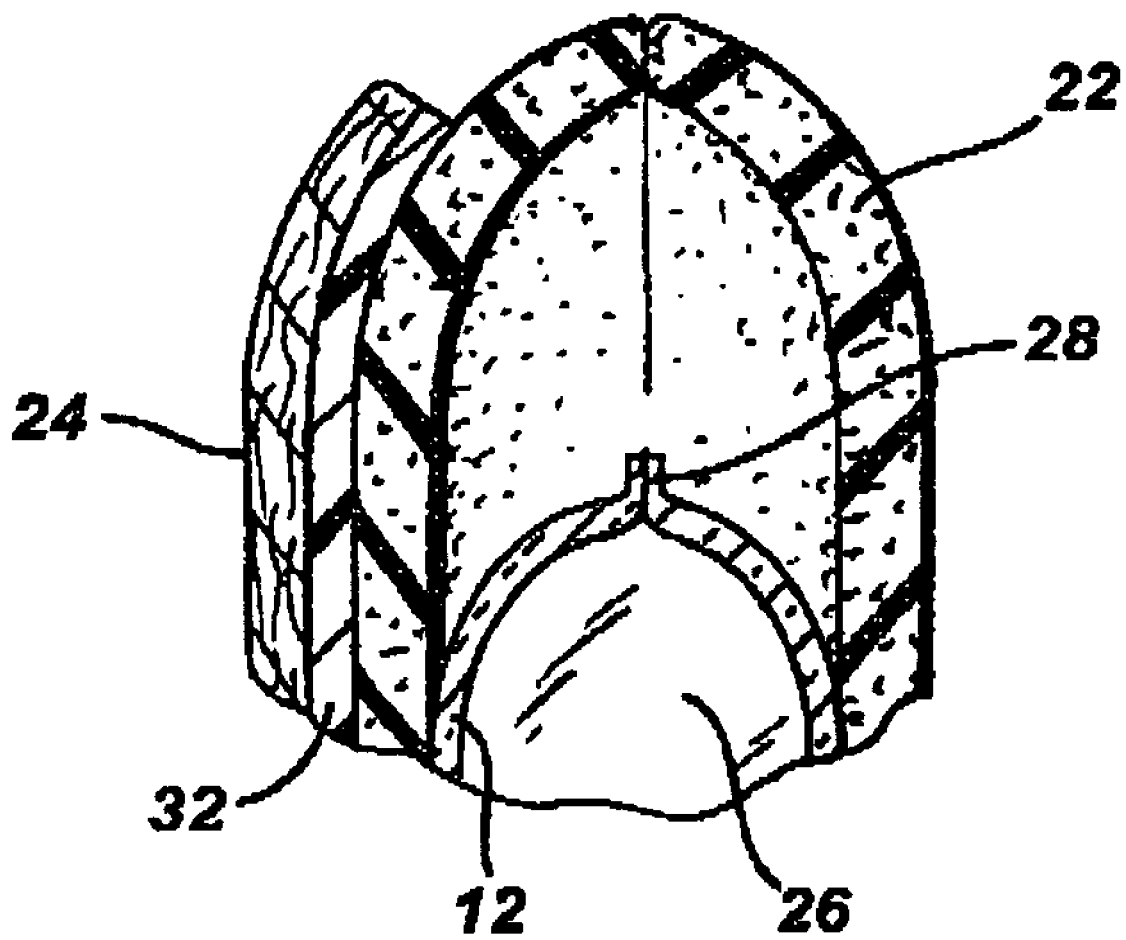
FIG. 4 is an enlarged cross-sectional view of the circled portion of FIG. 3.
Figure 5:
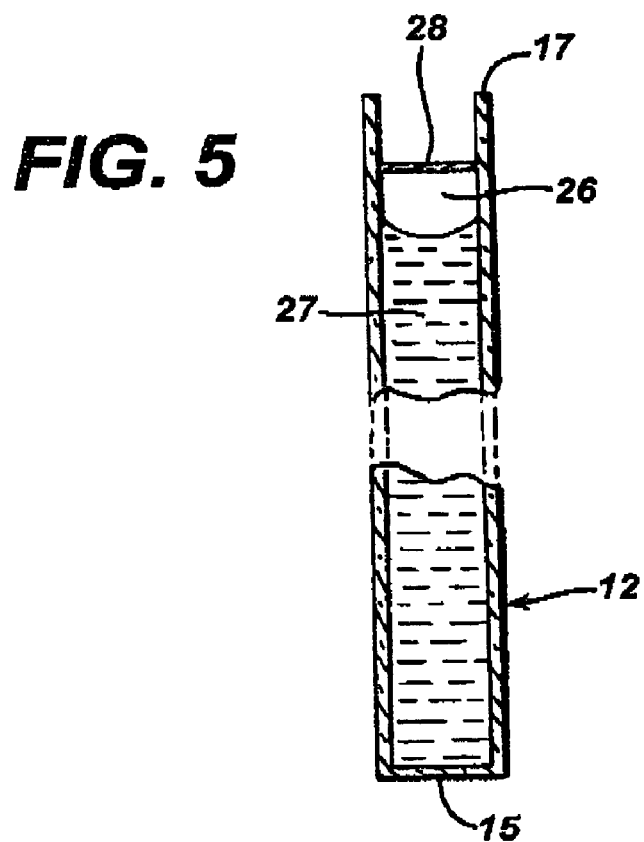
FIG. 5 is a greatly enlarged cross-sectional view of a portion of the swab.

Wound treating element 20 is secured to stick 12 at its distal portion 16. Wound treating element 20 comprises a wound cleaning element 22 and a hemostat-containing element 24. In the embodiment under discussion, and as seen in FIGS. 3 and 4 of the drawings, wound cleansing element 22 is in the shape of a tear-drop and is attached over distal end 17 of stick 12 and continued downwardly over the upper part of distal portion 16. Wound cleansing element 22 may be secured to the outer surface of stick 12 by frictional engagement; alternatively, an adhesive (not shown in the drawings) may be used for this purpose.

Figure 6:
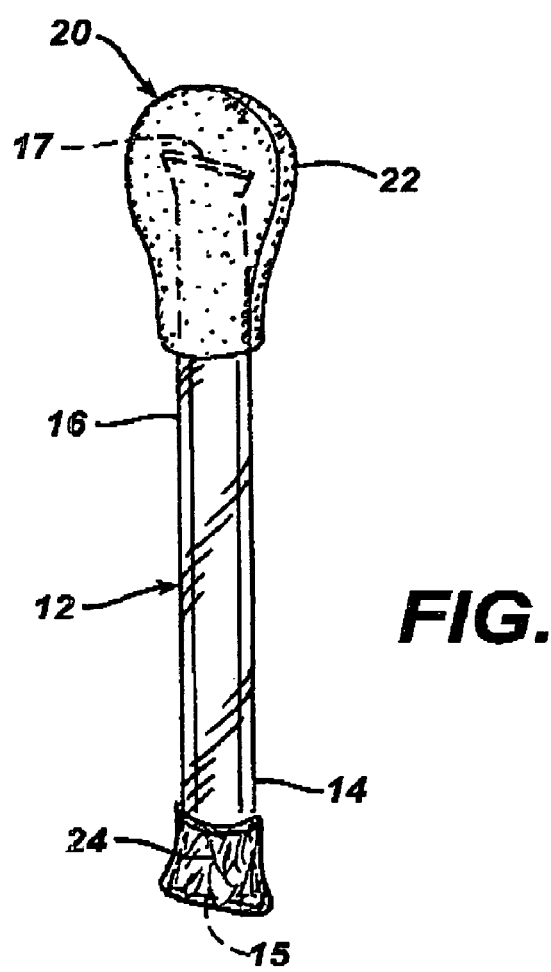
FIG. 6 is a perspective view of a second embodiment of a swab according to the present invention.

Also as illustrated in FIGS. 3 and 4, hemostat-containing element 24 is secured to the outer surface of one side of wound cleansing element 22. Preferably, a liquid impermeable material in the form of a thin layer of liquid impermeable film 32 is placed between the adjoining surfaces of the wound cleansing element and the hemostat-containing element. The presence of liquid impermeable film 32 prevents liquid released to wound cleansing element 22 during use from undesirably flowing into hemostat-containing element 24. Film 32 need not be used if it is not necessary to restrict flow of liquid from the wound cleansing element into the hemostat-containing element. It will be apparent to those skilled in the art that an adhesive can be used to secure element 24 to film 32 and to secure film 32 to element 22. Alternatively, film 32 can be heat-sealed to element 24 and the resulting heat sealed laminate can then be secured to element 22. It will be understood that, if so desired, the hemostat-containing element can be attached to the proximal portion 14 of stick 12. See FIG. 6.

The hollow interior of stick 12 defines a reservoir 26 for containing a liquid composition 27. The proximal end 15 of stick 12 is sealed to provide a liquid tight seal. The reservoir is completed by the provision of a frangible seal 28. Preferably, the frangible seal is provided at distal end 17 of stick 12. It will be understood that frangible seal 28 is liquid-tight prior to use of the swab. Further, it will be recognized that frangible seal 28 must be weaker than the seal at proximal end 15 of the stick. Thus, when stick 12 is manipulated, for example by squeezing with the fingers at the position indicated by the arrows in FIG. 3, frangible seal 28 will be broken while the seal at proximal end 15 will remain intact. Once frangible seal 28 is broken, the liquid in reservoir 26 can flow into wound cleansing element 22.

Where stick 12 is made of a plastic material, the plastic at the distal end 17 of the stick may be first thinned out and then sealed to provide frangible seal 28.

If it is decided to locate frangible seal 28 downwardly a distance from the distal end 17 of stick 12 toward proximal end 15 of the stick, that portion of stick 12 between the thus located frangible seal and distal end 17 must be hollow to permit the establishment of liquid communication between reservoir 26 and wound cleansing element 22 when frangible seal 28 is broken at the time of use. See FIG. 5.

Suitable sticks for use in the present invention are known in the art and are taught, for example, in U.S. Pat. No. 5,100,028, the disclosure of which is hereby incorporated by reference. Stick 12 may be made of any suitable material including, but not limited to, plastics such as polyethylene, polypropylene, and the like, and paper. The size of the stick is not critical. The size of the liquid reservoir is sufficient to retain enough liquid for cleansing or otherwise treating a wound.

Frangible seals are known in the art. Suitable frangible seals may be made from silicone materials, waxes, thin polymeric films and the like. When the consumer wants the liquid to flow to the pad, the stick is squeezed with the consumer's fingers. When enough force is generated from squeezing the stick, the frangible seal is disrupted, thereby permitting flow of the liquid to the wound cleansing element.

Suitable liquids for use in the liquid reservoir include, but are not limited to, wound cleansing solutions, antiseptic solutions, anesthetic solutions, antibiotic solutions, solutions of anti-inflammatory agents, mixtures thereof, and the like.

Suitable substrate materials for the wound cleansing element include woven fabrics, nonwoven fabrics, gauze, foams, sponges, and the like. The size of the wound cleansing element is not critical, but should be sufficient to provide for effective cleansing of the wound.

Suitable substrate materials for the hemostat-containing element include woven fabrics, nonowoven fabrics, gauze, foams, sponges and the like. The hemostat-containing element includes a hemostatic agent. Alginate salts are useful hemostatic agents. Suitable alginate salts include, but are not limited to, sodium alginate, calcium alginate, potassium alginate, and ammonium alginate. Other hemostatic materials include, but are not limited to, collagen, fibrin, thrombin, potato starch, bismuth subgallate, sodium hypochloride, chitosan and oxidized celluloses, including oxidized celluloses in fibrous form. The hemostatic agent may be coated onto, dusted onto or impregnated into the substrate material used for the hemostat-containing element. In addition, the hemostat may be formed into fibers which are then incorporated into the hemostat-containing substrate.

Suitable materials for making liquid impermeable film 32 include polyolefins, such as polyethylene and polypropylene; polyvinyl acetate; and the like. The wound cleansing element may be joined to the hemostat-containing element by such means as air entanglement, adhesives, ultrasonic welding, heat bonding, and the like. When a barrier film is utilized, an adhesive may be coated onto the barrier and the wound cleansing element and the hemostat-containing element may then be secured to the adhesive coated barrier film.

The example set forth below further illustrates the nature of the invention and the manner of carrying it out. However, the invention should not be considered as being limited to the details thereof.

EXAMPLE

A Puritan Brand Self-Saturating swab (Puritan Medical Products Company

Item #4620) was purchased. The swab was 4½ inches long and had a popule type shaft and a foam tip. The popule shaft was filled with 70% isopropyl alcohol as an antiseptic agent.

A Johnson & Johnson Brand First Aid Advanced Care Quick Stop Guaze Pad (containing calcium alginate fibers as a hemostat) was cut to the same size and shape as the foam tip of the swab.

The cut gauze pad was attached to the swab tip using double sided tape such that the gauze backing (smooth side) was adhered to the foam tip and the hemostatic fibers were exposed. When the shaft of the swab is squeezed, the isopropyl alcohol is forced into the foam tip portion of the swab and can be used to cleanse a wound. The alginate fiber gauze pad can be used to stop the wound from bleeding.

We claim:

1. A hemostatic wound cleansing swab comprising a stick and a wound treating element, said stick comprising a proximal portion, a proximal end, a distal portion, a distal end and a reservoir for containing a liquid, said wound treating element being secured to said distal portion and comprising a cleansing element for cleansing a wound and a hemostatic element for effecting hemostasis of a wound, said reservoir being in fluid communication with said cleansing element, wherein said hemostatic element is discrete from said cleansing element.

2. The swab of claim 1 wherein said stick is hollow and said reservoir is formed by a liquid-tight seal located substantially at the proximal end of said stick and a liquid-tight, frangible seal located in the distal portion of said stick.

3. The swab of claim 2 wherein said frangible seal is located substantially at the distal end of said stick.

4. The swab of claim 1 wherein said reservoir contains a liquid selected from the group consisting of wound cleansing solutions, antiseptic solutions, anesthetic solutions, antibiotic solutions, solutions of anti-inflammatory agents, and mixtures thereof.

5. The swab of claim 4 wherein said liquid is a wound cleansing solution.

6. The swab of claim 1 wherein said hemostatic element comprises a substrate material and a hemostatic agent.

7. The swab of claim 6 wherein said substrate material is selected from the group consisting of woven fabrics, non-woven fabrics, gauze, foams and sponges.

8. The swab of claim 7 wherein said substrate material is a foam.

9. The swab of claim 1 wherein said hemostatic element comprises a hemostatic material selected from the group consisting of alginate salts, collagen, fibrin, thrombin, potato starch, bismuth subgallate, sodium hypochloride, oxidized celluloses and chitosan.

10. The swab of claim 9 wherein said hemostatic material is an alginate salt.

11. The swab of claim 9 wherein said hemostatic material is oxidized cellulose fiber.

12. The swab of claim 9 wherein a liquid impermeable film is placed between said cleansing element and said hemostatic element.

13. The swab of claim 1 wherein said reservoir contains a liquid for application to a wound.

14. A swab for use in treating a wound, said swab comprising:
    a stick having a proximal portion, a proximal end, a distal portion and a distal end;
    a reservoir for containing a liquid;
    a hemostatic element for effecting hemostasis of a wound;
    an element for applying said liquid to a wound being secured to one of said proximal and distal portions, said element for applying said liquid being discreet from said hemostatic element;
    said hemostatic element being secured to the other of said proximal and distal portions;
    said reservoir being in fluid communication with said element for applying said liquid to said wound.

15. The swab of claim 1 further comprising a liquid impermeable film disposed between said cleansing element and said hemostatic element.

* * * * *